(12) United States Patent
Yang et al.

(10) Patent No.: US 10,894,761 B2
(45) Date of Patent: Jan. 19, 2021

(54) RECYCLABLE CLEAN FRACTURING FLUID THICKENER, PREPARATION METHOD AND RECOVERY METHOD THEREOF, AND HIGH-TEMPERATURE RESISTANT CLEAN FRACTURING FLUID

(71) Applicant: SOUTHWEST PETROLEUM UNIVERSITY, Sichuan (CN)

(72) Inventors: Xiaojiang Yang, Sichuan (CN); Jincheng Mao, Sichuan (CN); Heng Zhang, Sichuan (CN)

(73) Assignee: SOUTHWEST PETROLEUM UNIVERSITY, Chengdu (CN)

( * ) Notice: Subject to any disclaimer, the term of this patent is extended or adjusted under 35 U.S.C. 154(b) by 0 days.

(21) Appl. No.: 16/937,529

(22) Filed: Jul. 23, 2020

(65) Prior Publication Data
US 2020/0354310 A1  Nov. 12, 2020

Related U.S. Application Data

(63) Continuation of application No. PCT/CN2018/105595, filed on Sep. 13, 2018.

(30) Foreign Application Priority Data

Aug. 17, 2018  (CN) .......................... 2018 1 0942253

(51) Int. Cl.
*C07C 233/36* (2006.01)
*C09K 8/68* (2006.01)

(52) U.S. Cl.
CPC .............. *C07C 233/36* (2013.01); *C09K 8/68* (2013.01); *C09K 2208/26* (2013.01)

(58) Field of Classification Search
None
See application file for complete search history.

(56) References Cited

U.S. PATENT DOCUMENTS 6,121,222 A  9/2000  Li et al.

FOREIGN PATENT DOCUMENTS

| CN | 102181279 | * | 9/2011 |
| CN | 102181279 | A | 9/2011 |
| CN | 103508913 | A | 1/2014 |

(Continued)

OTHER PUBLICATIONS

Xiaojia Xue et al. Synthesis and application of organic boron crosslinker YL-J for polyvinyl alcohol fracturing fluid, Jul. 2013, No. 4, vol. 28.

(Continued)

*Primary Examiner* — Amy C Bonaparte
(74) *Attorney, Agent, or Firm* — Wayne & Ken, LLC; Tony Hom (57) ABSTRACT

Disclosed are a recyclable clean fracturing fluid thickener, a preparation method and a recovery method thereof, and a high-temperature resistant clean fracturing fluid, which relate to the stimulation treatment of oil and gas fields. Diethanolamine and thionyl chloride are used as raw materials and reacted to obtain an intermediate, which is then reacted with an unsaturated fatty acid amidopropyl dimethylamine to produce the recyclable clean fracturing fluid thickener. The clean fracturing fluid can be used in the fracturing stimulation treatment of low and medium permeability reservoirs.

16 Claims, 6 Drawing Sheets

(56) References Cited

FOREIGN PATENT DOCUMENTS

| CN | 103508914 | A | | 1/2014 |
|---|---|---|---|---|
| CN | 105086986 | A | | 11/2015 |
| CN | 106167506 | A | | 11/2016 |
| CN | 106947455 | | * | 7/2017 |
| CN | 106947455 | A | | 7/2017 |
| CN | 111040103 | A | | 4/2020 |
| WO | 2011092221 | A1 | | 8/2011 |
| WO | 2014011695 | A2 | | 1/2014 |

OTHER PUBLICATIONS

Hongxia Li et al. Synthesis of a new-type germicide of biquaternary ammonium salt, Apr. 2015, No. 4, vol. 23.

* cited by examiner

RECYCLABLE CLEAN FRACTURING FLUID THICKENER, PREPARATION METHOD AND RECOVERY METHOD THEREOF, AND HIGH-TEMPERATURE RESISTANT CLEAN FRACTURING FLUID

CROSS-REFERENCE TO RELATED APPLICATIONS

This application is a continuation of International Patent Application No. PCT/CN2018/105595, filed on Sep. 13, 2018, which claims the benefit of priority from Chinese Patent Application No. 201810942253.9, filed on Aug. 17, 2018. The content of the aforementioned applications, including any intervening amendments thereto, is incorporated herein by reference in its entirety.

TECHNICAL FIELD

The disclosure relates to the preparation of a fracturing fluid thickener, which is a viscoelastic surfactant, particularly to a Gemini quaternary ammonium cationic viscoelastic surfactant for the exploitation of oil and gas resources, and more specifically to a recyclable clean fracturing fluid thickener, a preparation method and recovery method thereof, and a high-temperature resistant clean fracturing fluid.

BACKGROUND

As a widely used reservoir stimulation technology, hydraulic fracturing is employed to change the radial flow near the wellbore to an approximately linear flow mainly by forming high-conductivity fractures around the wellbore, which not only can reduce the filtration resistance of the fluid near the wellbore, but also can increase the drainage area of the oil and gas well, improving the production of the oil and gas well. Recently, with the increase in the proportion of low-permeability, ultra-low-permeability, tight oil and gas reservoirs, and unconventional oil and gas reserves, there are about 70% of oil wells and 90% of gas wells required to be fractured before the exploitation, so the fracturing stimulation has gradually played an indispensable role in promoting the production of oil and gas resources.

During the fracturing process, the fracturing fluid, as a carrier for transmitting pressure and delivering a proppant, will greatly affect the entire fracturing construction. Currently, the most widely used fracturing fluid system is a polymer fracturing fluid such as boron-crosslinked guar gum and its derivatives.

However, it has been found through extensive on-site applications and researches that the use of fracturing fluid with guar gum or a derivative thereof as a thickener in the fracturing stimulation will raise several problems, for example, the adsorption of macromolecules adsorb will block the seepage channels in the formation; the gel breaker residues will block the proppant-packed layer; and a filter cake damage may occur. Considering the above-mentioned problems, extensive researches have been conducted in recent decades, but it still fails to effectively overcome the blockage caused by the macromolecule adsorption and the alkaline fluid invasion damage.

The development of a clean fracturing fluid system using a viscoelastic surfactant as the thickener successfully solves the above problems, but the existing viscoelastic surfactants are greatly limited in the promotion due to unsatisfactory temperature resistance and high cost. So far, there are merely less than 10% of the oil and gas wells involving the use of a clean fracturing fluid. Moreover, the environmental pollution associated with hydraulic fracturing has received more and more attention worldwide, and thus the flowback of the fracturing fluid has become an indispensable treatment in the current hydraulic fracturing process.

Therefore, there is an urgent need to develop a recyclable clean fracturing fluid thickener with high-temperature resistance and low cost.

SUMMARY

To solve the problems in the prior art, the disclosure provides a recyclable clean fracturing fluid thickener, a preparation method and a recovery method thereof, and a high-temperature resistant clean fracturing fluid. The disclosure not only provides a clean fracturing fluid with high-temperature resistance and low cost, but also designs a recovery method of the fracturing fluid thickener to improve the treatment of a fracturing flow-back fluid, avoiding environmental pollution.

The technical solutions of the disclosure are illustrated as follows.

In a first aspect, the disclosure provides a recyclable clean fracturing fluid thickener with the following structural formula:

wherein R is an unsaturated hydrocarbon chain having 17-21 carbon atoms.

The recyclable clean fracturing fluid thickener has a small molecular weight, and the clean fracturing fluid containing the recyclable clean fracturing fluid thickener has good resistance to high temperature (up to 160° C.). There is no residue left after the gel breaking, and the thickener is recyclable, which can reduce the cost and promote the harmless treatment of fracturing flowback fluid.

In a second aspect, the disclosure provides a method of preparing the above recyclable clean fracturing fluid thickener, comprising:

(1) dissolving diethanolamine and thionyl chloride in chloroform to obtain a diethanolamine solution and a thionyl chloride solution, respectively; dropwise adding the thionyl chloride solution to the diethanolamine solution in an ice bath to perform a reaction; and after the reaction is completed, cooling the reaction mixture to produce an intermediate; as shown in the following reaction scheme:

wherein the intermediate is a white hydrochloride solid and is obtained by cooling precipitation; and (2) mixing the intermediate with an unsaturated fatty acid amidopropyl dimethylamine to produce a mixture; dissolving the mixture with ethanol; reacting the reaction mixture under heating; filtering the reaction mixture to obtain a filtrate; and distilling the filtrate under vacuum to produce the fracturing fluid thickener; as shown in the following reaction scheme:

wherein the fracturing fluid thickener is a yellow gelatinous product.

In an embodiment, in step (1), a reaction temperature is 30-50° C.; a reaction time is 4.5-5.5 h; and a molar ratio of diethanolamine to thionyl chloride is 1:(2.0-2.4).

In an embodiment, in step (2), a reaction temperature is 70-90° C.; a reaction time is 23.5-24.5 h; and a molar ratio of the intermediate to the unsaturated fatty acid amidopropyl dimethylamine is 1:(2.0-2.2).

Diethanolamine and thionyl chloride are used as raw materials to obtain an intermediate, which is then reacted with an unsaturated fatty acid amidopropyl dimethylamine to obtain the recyclable clean fracturing fluid thickener. The preparation method has simple operation, and the prepared thickener enables the clean fracturing fluid to maintain excellent viscoelasticity below 160° C., so the fracturing fluid can be used in the fracturing stimulation treatment for low and medium permeability reservoirs. The recyclable clean fracturing fluid thickener can be recovered from the gel-breaking product by phase separation, facilitating the green and clean fracturing operation. The fracturing fluid provided herein has advantages of high-temperature resistance and easy preparation, and the thickener used therein can be recycled by phase separation, further promoting the treatment of hydraulic fracturing flowback fluid and avoiding environmental pollution.

In an embodiment, in step (1), the reaction temperature is 35-45° C. and the reaction time is 4.8-5.2 h.

In an embodiment, in step (1), the reaction temperature is 40° C., and the reaction time is 5 h.

In an embodiment, in step (2), the reaction temperature is 75-85° C., and the reaction time is 23.8-24.2 h.

In an embodiment, in step (2), the reaction temperature is 80° C., and the reaction time is 24 h.

In some embodiments, the unsaturated fatty acid is palmitic acid, oleic acid or erucic acid.

In a third aspect, the disclosure further provides a method of recovering the recyclable clean fracturing fluid thickener from a fracturing fluid, comprising:

(1) subjecting a fracturing fluid containing the fracturing fluid thickener to gel breaking to produce a gel-breaking product;

(2) adding an acid solution to the gel-breaking product obtained in step (1) for phase separation; and (3) collecting an upper solid phase to recover the fracturing fluid thickener.

A high-temperature resistant clean fracturing fluid system prepared using the above recyclable clean fracturing fluid thickener has a viscosity of 40 mPa·s at 160° C., which is greater than the industrial standard 25 mPa·m. Moreover, the thickener can be recovered from the gel-breaking product by phase separation, which involves the simple operation and a recovery rate as high as 100%. The thickener still has excellent performance after multiple recoveries.

In an embodiment, the acid solution is hydrogen chloride, sulfuric acid, phosphoric acid, or carbonic acid.

In a fourth aspect, the disclosure also provides a high-temperature resistant clean fracturing fluid, comprising: an inorganic salt and the above recyclable clean fracturing fluid thickener.

In an embodiment, the inorganic salt is potassium chloride, sodium chloride, potassium bromide, sodium bromide or sodium salicylate.

The fracturing fluid may further include other substances according to industry standard and actual requirement, and there are no special limitations for the mixing ratio between the raw materials and the preparation process.

The beneficial effects of the disclosure are illustrated as follows.

The method provided herein of preparing the recyclable clean fracturing fluid thickener has a simple process, high yield (generally up to 98%), and low impurity content. The impurities have less effect on the product performance, and thus it is not required to perform purification.

The recyclable clean fracturing fluid thickener prepared herein has a critical micelle concentration of $1-2\times10^{-4}$ mol/L, which is 1-2 orders of magnitude lower than that of the conventional single-tail viscoelastic surfactant, providing a better thickening effect.

The high-temperature resistant clean fracturing fluid prepared using the recyclable clean fracturing fluid thickener synthesized herein has simple and rapid preparation, which is performed merely through steps of: dissolving the required inorganic salt and the thickener with a certain amount of water, respectively; and mixing the two solutions uniformly.

The recyclable clean fracturing fluid thickener provided herein can be recovered from a fracturing fluid system containing the same by phase separation after the gel breaking, and the recovery rate can reach 100%.

DETAILED DESCRIPTION OF EMBODIMENTS

The principles and features of the disclosure will be described below with reference to the accompanying drawings and embodiments. These embodiments are merely illustrative of the disclosure, and are not intended to limit the disclosure. Unless otherwise specified, the process in the following embodiments is carried out under conventional conditions or the conditions recommended by the manufacturer. Unless otherwise specified, the reagents or instruments used below are all commercially available.

The unsaturated fatty acid used in the following embodiments is exemplified by oleic acid. In some embodiments, the unsaturated fatty acid may be palmitic acid or erucic acid.

Example 1

Provided herein was a method of preparing a recyclable clean fracturing fluid thickener, which was specifically described as follows.

Diethanolamine was added to a round-bottomed flask, to which chloroform was added to dissolve the diethanolamine to produce a diethanolamine solution. Thionyl chloride was dissolved in a certain amount of chloroform and dropwise added to the diethanolamine solution in an ice-water bath. After the dropwise adding was completed, the reaction mixture was heated in an oil bath to 30° C. and refluxed for 5.5 h, where a molar ratio of diethanolamine to thionyl chloride was 1:2. After the reaction was completed, the reaction mixture was cooled to 20° C. to produce a white hydrochloride intermediate A. Then the intermediate A and N, N-dimethyloleoaminde propylamine were added to a flask, dissolved with an appropriate amount of ethanol, heated to 70° C. and reacted for 24.5 h, where a molar ratio of the intermediate A to N, N-dimethyloleoaminde propylamine was 1:2. The reaction mixture was filtered, and the filtrate was distilled under vacuum to produce a yellow gelatinous thickener.

Example 2

Provided herein was a method of preparing a recyclable clean fracturing fluid thickener, which was specifically described as follows.

Diethanolamine was added to a round-bottomed flask, to which chloroform was added to dissolve the diethanolamine to produce a diethanolamine solution. Thionyl chloride was dissolved in a certain amount of chloroform and dropwise added to the diethanolamine solution in an ice-water bath. After the dropwise adding was completed, the reaction mixture was heated in an oil bath to 50° C. and refluxed for 4.5 h, where a molar ratio of diethanolamine to thionyl chloride was 1:2.2. After the reaction was completed, the reaction mixture was cooled to 20° C. to produce a white hydrochloride intermediate A. Then the intermediate A and N, N-dimethyl oleoaminde propylamine were added to a flask, dissolved with an appropriate amount of ethanol, heated to 90° C. and reacted for 23.5 h, where a molar ratio of the intermediate A to N, N-dimethyloleoaminde propylamine was 1:2.1. The reaction mixture was filtered, and the filtrate was distilled under vacuum to produce a yellow gelatinous thickener.

Example 3

Provided herein was a method of preparing a recyclable clean fracturing fluid thickener, which was specifically described as follows.

Diethanolamine was added to a round-bottomed flask, to which chloroform was added to dissolve the diethanolamine to produce a diethanolamine solution. Thionyl chloride was dissolved in a certain amount of chloroform and dropwise added to the diethanolamine solution in an ice-water bath. After the dropwise adding was completed, the reaction mixture was heated in an oil bath to 35° C. and refluxed for 5.2 h, where a molar ratio of diethanolamine to thionyl chloride was 1:2.4. After the reaction was completed, the reaction mixture was cooled to 20° C. to produce a white hydrochloride intermediate A. Then the intermediate A and N, N-dimethyloleoaminde propylamine were added to a flask, dissolved with an appropriate amount of ethanol, heated to 75° C. and reacted for 24.2 h, where a molar ratio of the intermediate A to N, N-dimethyloleoaminde propylamine was 1:2.2. The reaction mixture was filtered, and the filtrate was distilled under vacuum to produce a yellow gelatinous thickener.

Example 4

Provided herein was a method of preparing a recyclable clean fracturing fluid thickener, which was specifically described as follows.

Diethanolamine was added to a round-bottomed flask, to which chloroform was added to dissolve the diethanolamine to produce a diethanolamine solution. Thionyl chloride was dissolved in a certain amount of chloroform and dropwise added to the diethanolamine solution in an ice-water bath. After the dropwise adding was completed, the reaction mixture was heated in an oil bath to 45° C. and refluxed for 4.8 h, where a molar ratio of diethanolamine to thionyl chloride was 1:2.4. After the reaction was completed, the reaction mixture was cooled to 20° C. to produce a white hydrochloride intermediate A. Then the intermediate A and N, N-dimethyloleoaminde propylamine were added to a flask, dissolved with an appropriate amount of ethanol, heated to 85° C. and reacted for 23.8 h, where a molar ratio of the intermediate A to N, N-dimethyloleoaminde propylamine was 1:2.2. The reaction mixture was filtered, and the filtrate was distilled under vacuum to produce a yellow gelatinous thickener.

Example 5

Provided herein was a method of preparing a recyclable clean fracturing fluid thickener, which was specifically described as follows.

Diethanolamine was added to a round-bottomed flask, to which chloroform was added to dissolve the diethanolamine to produce a diethanolamine solution. Thionyl chloride was dissolved in a certain amount of chloroform and dropwise added to the diethanolamine solution in an ice-water bath. After the dropwise adding was completed, the reaction mixture was heated in an oil bath to 40° C. and refluxed for 5 h, where a molar ratio of diethanolamine to thionyl chloride was 1:2.4. After the reaction was completed, the reaction mixture was cooled to 20° C. to produce a white hydrochloride intermediate A. Then the intermediate A and N, N-dimethyloleoaminde propylamine were added to a flask, dissolved with an appropriate amount of ethanol, heated to 80° C. and reacted for 24 h, where a molar ratio of the intermediate A to N, N-dimethyloleoaminde propylamine was 1:2.2. The reaction mixture was filtered, and the filtrate was distilled under vacuum to produce a yellow gelatinous thickener Example 6

Figure 1:
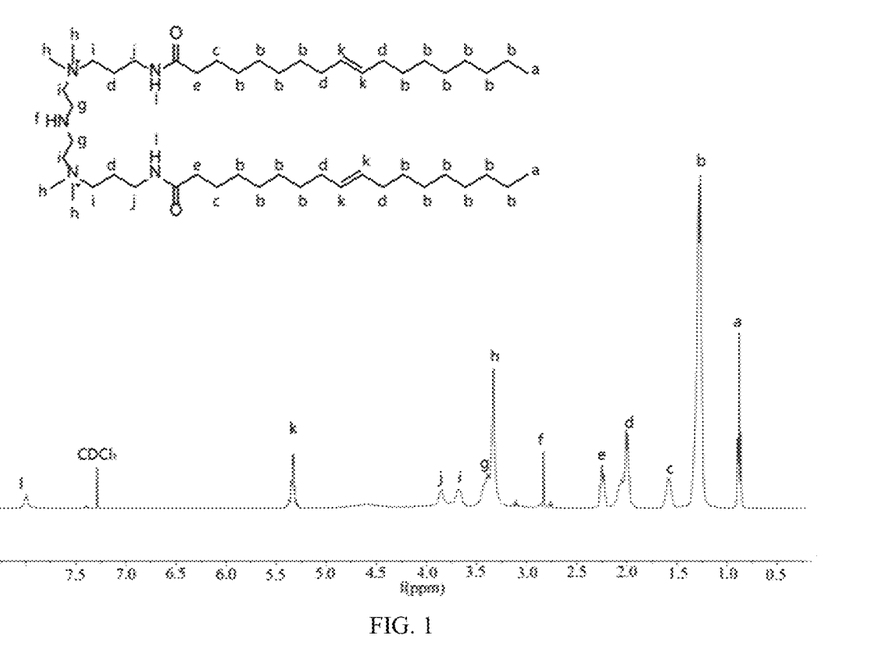
FIG. 1 shows a molecular structure and 1H-NMR spectrum of a thickener prepared in Example 6 of the disclosure.

Diethanolamine was added to a round-bottomed flask, to which chloroform was added to dissolve the diethanolamine to produce a diethanolamine solution. Thionyl chloride was dissolved in a certain amount of chloroform and dropwise added to the diethanolamine solution in an ice-water bath. After the dropwise adding was completed, the reaction mixture was heated in an oil bath to 40° C. and refluxed for 5 h, where a molar ratio of diethanolamine to thionyl chloride was 1:2.05. After the reaction was completed, the reaction mixture was cooled to 20° C. to produce a white hydrochloride intermediate A. Then the intermediate A and N, N-dimethyloleoaminde propylamine were added to a flask, dissolved with an appropriate amount of ethanol, heated to 80° C. and reacted for 24 h, where a molar ratio of the intermediate A to N, N-dimethyloleoaminde propylamine was 1:2.05. The reaction mixture was filtered, and the filtrate was distilled under vacuum to produce a yellow gelatinous thickener In order to further improve the purity of the thickener, ethyl acetate was used herein to crystallize the crude product for purification, and the crystallized product had a purity of 99% or more. The molecular structure and 1H-NMR of the obtained thickener were shown in FIG. 1.

Experimental Example 1

Figure 2:
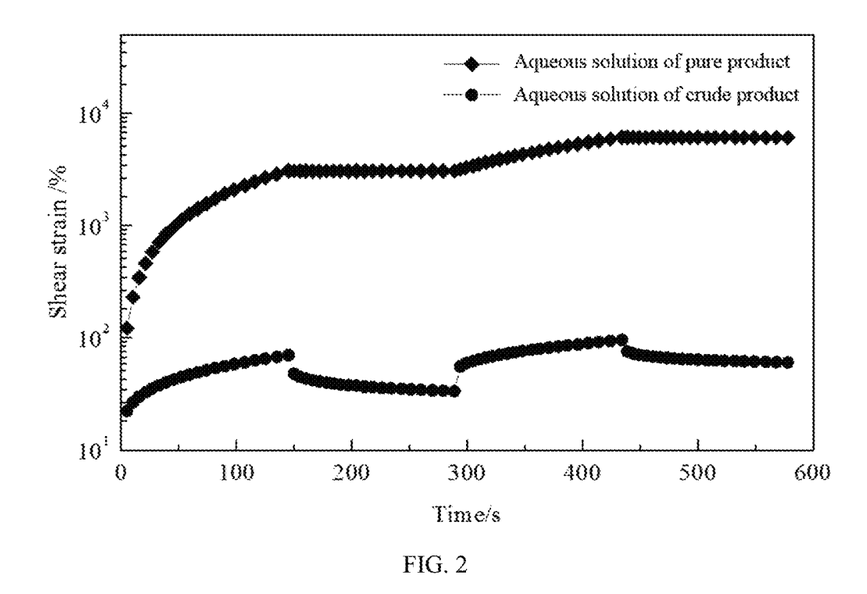
FIG. 2 shows the comparison between the aqueous solutions of a crude thickener product and a pure thickener product in the creep recovery and proppant-suspending performance according to Experimental Example 1 of the disclosure.

The crude thickener product obtained in Example 5 and its purified product (the purification was performed according to the above process) were tested for the creep recovery and proppant-suspending property, and the results were shown in FIG. 2 and Table. 1. The results demonstrated that the aqueous solution prepared from the crude product had better proppant-suspending property, indicating that the synthesized product did not need to be purified, and the conversion rate of the raw material was 100%.

TABLE 1

| Proppant-suspending property of the thickener products before and after purification | | | | | | | | | | |
|---|---|---|---|---|---|---|---|---|---|---|
| Product Concentration | J-22 (Before purification) | | | | | J-22 (After purification) | | | | |
| (%) | 1 | 2 | 3 | 4 | 5 | 1 | 2 | 3 | 4 | 5 |
| Settling time (s) | 15.7 | / | / | / | / | 1.26 | 1.58 | 2.26 | 4.24 | 7.57 |
|  | 15.69 | / | / | / | / | 1.45 | 1.34 | 2.57 | 4.35 | 7.66 |
|  | 19.99 | / | / | / | / | 1.32 | 1.46 | 2.48 | 4.42 | 7.32 |
|  | 18.26 | / | / | / | / | 1.26 | 1.55 | 2.62 | 4.47 | 7.44 |
|  | 16.36 | / | / | / | / | 1.46 | 1.43 | 2.54 | 4.55 | 7.54 |
|  | 17.1 | / | / | / | / | 1.51 | 1.51 | 2.47 | 4.38 | 7.69 |
|  | 17.2 | / | / | / | / | 1.55 | 1.46 | 2.55 | 4.42 | 7.78 |
|  | 15.95 | / | / | / | / | 1.43 | 1.53 | 2.61 | 4.67 | 7.33 |
| Average settling time (s) | 17.03 | / | / | / | / | 1.41 | 1.48 | 2.51 | 4.44 | 7.54 |
| Settling speed (cm/s) | 1.47 | / | / | / | / | 17.79 | 16.86 | 9.95 | 5.63 | 3.32 |

Notes:
Proppant: 20-40 mesh ceramsite (375-750 μm);
Settling height: 25 cm;
Temperature: room temperature;
"/" means the ceramsite does not settle.

Experimental Example 2

The surfactant prepared in Example 5 was tested to have a critical micelle concentration of $1.47 \times 10^{-4}$ mol/L, and then the surfactant was used as a thickener to prepare a fracturing fluid containing 3.7% by weight of the thickener, 0.25% by weight of KCl and 0.1% by weight of KBr.

Figure 3:
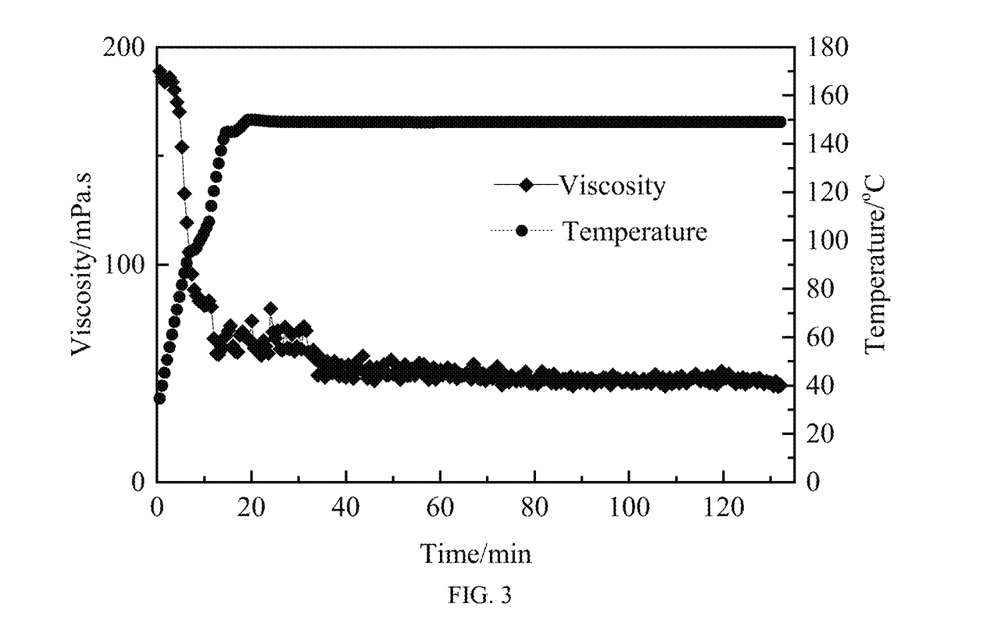
FIG. 3 shows the test results of the rheological property of the fracturing fluid prepared in Experimental Example 2 of the disclosure.
Figure 4:
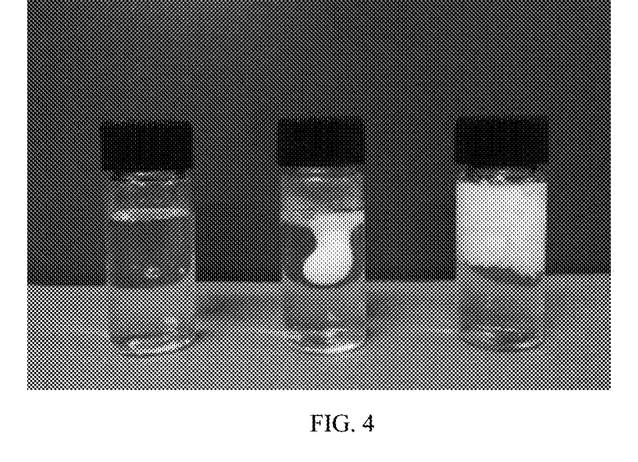
FIG. 4 shows the phase separation of the fracturing fluid system after gel breaking according to Experimental Example 2.

The above fracturing fluid was subjected to rheological property tests under the shearing conditions of 160° C. and 170 $s^{-1}$, and the test results were shown in FIG. 3. As shown in FIG. 3, the fracturing fluid system prepared from the thickener provided herein had a resistance to a temperature of 160° C. Moreover, it also had an excellent proppant-suspending property. The fracturing fluid system was subjected to gel breaking with 30% kerosene, and the resulting gel-breaking product was free of residue. Then the gel-breaking product was added with 2% of hydrochloric acid, and a small number of white floccules were generated. The gel-breaking product was layered by standing for a while (as shown in FIG. 4), where the white floccule was recovered as the thickener with a recovery rate of 42%.

Experimental Example 3

Figure 5:
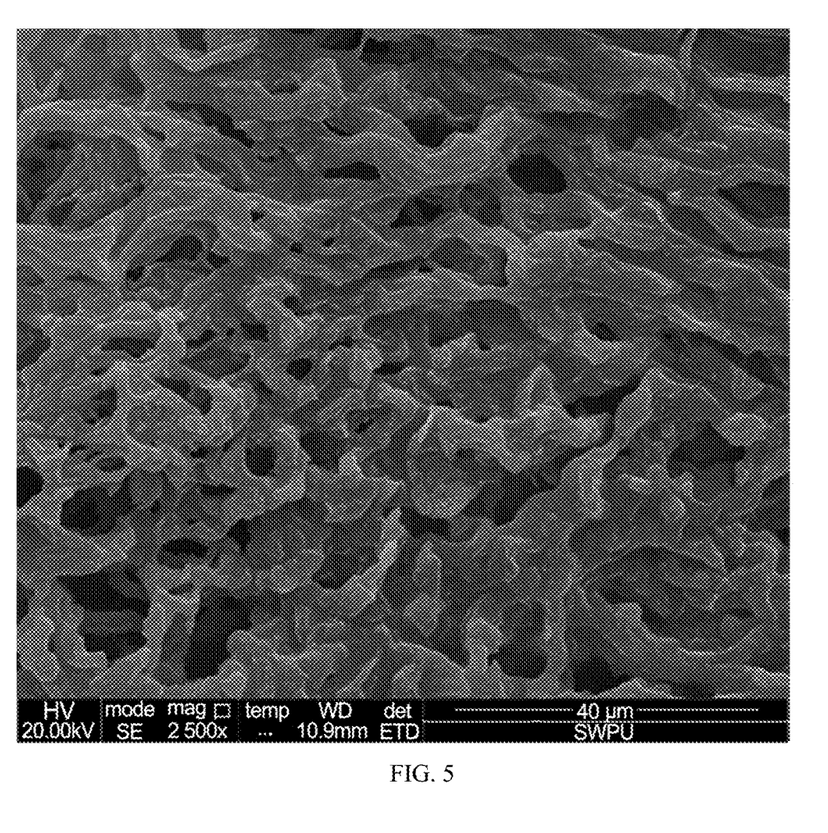
FIG. 5 is a scanning electron micrograph of the fracturing fluid prepared from the thickener recovered in Experimental Example 2 according to Experimental Example 3 of the disclosure.
Figure 6:
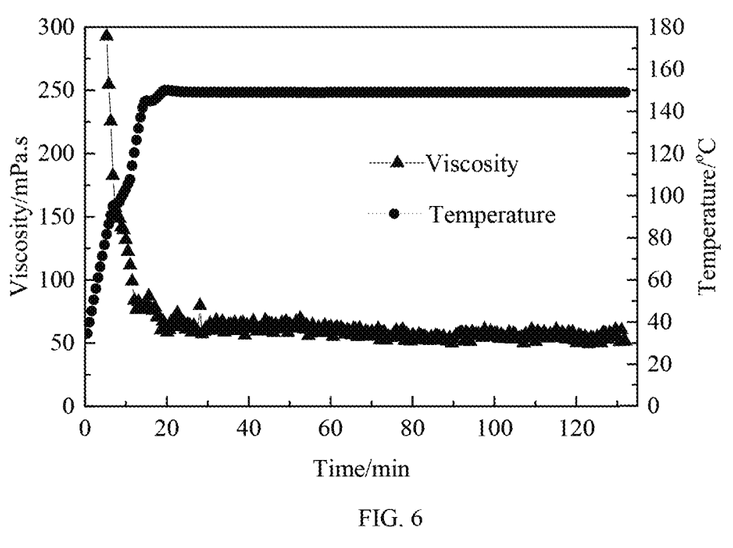
FIG. 6 shows the test results of the rheological property of the fracturing fluid prepared from the thickener recovered in Experimental Example 2 according to Experimental Example 3 of the disclosure.

The product recovered in Experimental Example 2 was again prepared into a fracturing fluid, which had an obvious micro-network structure (as shown in FIG. 5). The fracturing fluid was tested again for the rheological property under the conditions of 140° C. and 170 $s^1$, and the test results were shown in FIG. 6. It can be seen from FIGS. 5-6 that the thickener still had desirable performance when reused.

Experimental Example 4

The surfactant prepared in Example 6 was tested to have a critical micelle concentration of $1.47 \times 10^{-4}$ mol/L, and then the surfactant was used as a thickener to prepare a fracturing fluid containing 4% by weight of the thickener, 0.5% by weight of KCl and 0.15% by weight of KBr.

Figure 7:
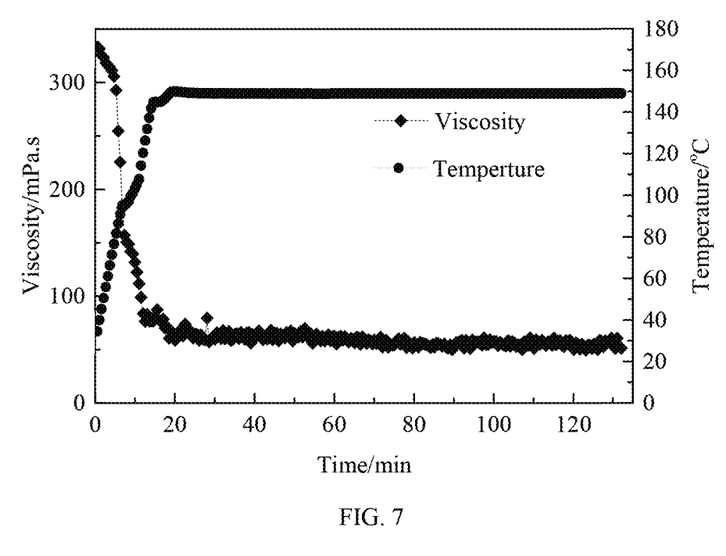
FIG. 7 shows the test results of the rheological property of the fracturing fluid prepared in Experimental Example 4 of the disclosure.
Figure 8:
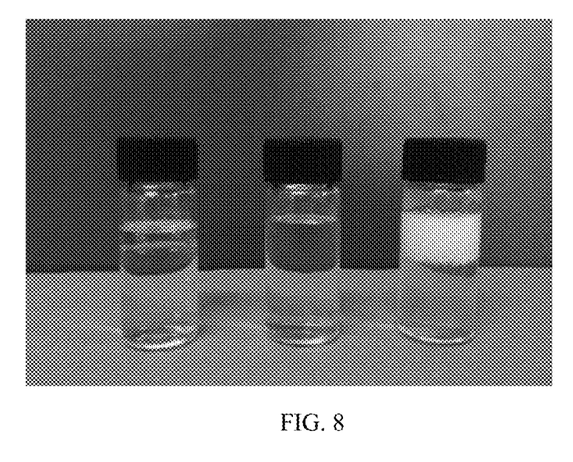
FIG. 8 illustrates the phase separation of the fracturing fluid system after gel breaking according to Experimental Example 4 of the disclosure.

The above fracturing fluid was subjected to the rheological property test under the shearing conditions of 160° C. and 170 $s^{-1}$, and the test results were shown in FIG. 7. As shown in FIG. 7, the fracturing fluid system showed resistance to the temperature of 160° C., and there was no obvious settlement in the 2-hour static proppant-suspending process, indicating that it had good proppant-suspending property. The fracturing fluid system was subjected to gel breaking with 30% kerosene, and the resulting gel-breaking product was free of residue. Then the gel-breaking product was added with 6% of hydrochloric acid, and a small number of white floccules were generated. The gel-breaking product was layered by standing for a while (as shown in FIG. 8), where the white floccule was recovered as the thickener with a recovery rate of 100%. It can be obtained from the comparison with Experimental Example 2 that the addition amount of hydrochloric acid significantly affected the recovery rate, specifically, when the hydrochloric acid content was increased from 2% (in Experimental Example 2) to 6%, the recovery rate was accordingly raised from 42% to 100%, indicating that the 6% hydrochloric acid can give rise to the best recovery effect.

Experimental Example 5

Figure 9:
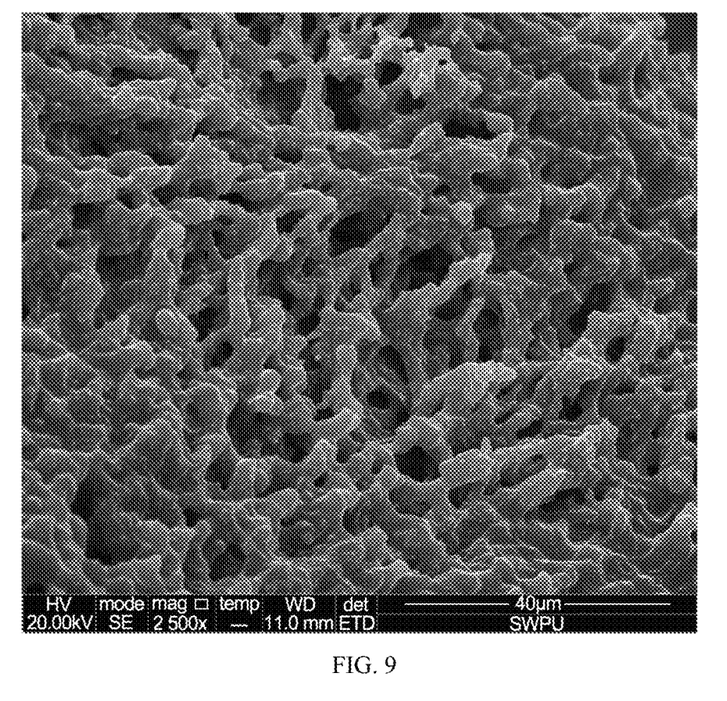
FIG. 9 is a scanning electron micrograph of the fracturing fluid prepared from the thickener recovered in Experimental Example 4 according to Experimental Example 5 of the disclosure.
Figure 10:
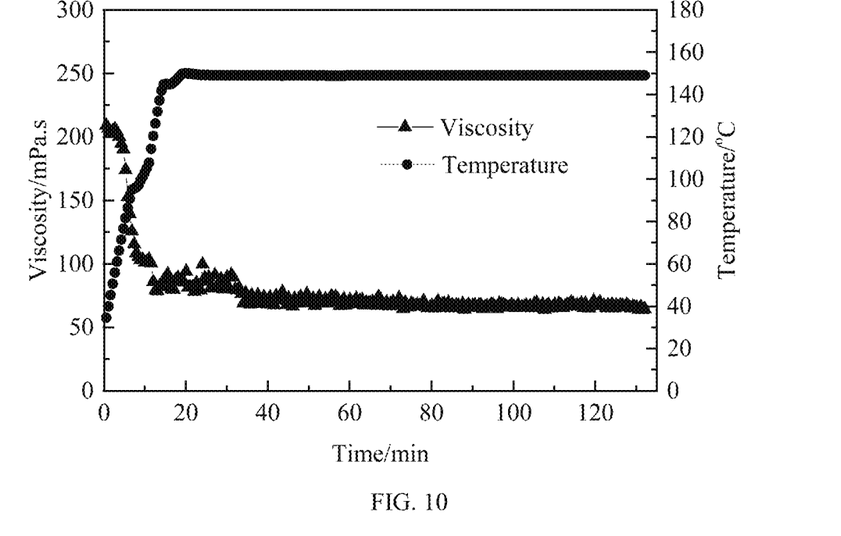
FIG. 10 shows the test results of the rheological property of the fracturing fluid prepared in Experimental Example 5 of the disclosure.

The product recovered in Experimental Example 4 was again prepared into a fracturing fluid, which had an obvious micro-network structure (as shown in FIG. 9). The fracturing fluid was tested again for the rheological property under the conditions of 140° C. and 170 $s^{-1}$, and the test results were shown in FIG. 10. It can be seen from FIGS. 9-10 that the fracturing fluid prepared from the recovered product still had good temperature resistance and micro-network structure.

Described above are only preferred embodiments of the disclosure, which are not intended to limit the disclosure. Any modification, replacement, and improvement made without departing from the spirit of the disclosure shall fall within the scope of the invention.

What is claimed is:

1. A fracturing fluid thickener of the following structural formula:

wherein R is an unsaturated hydrocarbon chain having 17-21 carbon atoms.

2. The fracturing fluid thickener of claim 1, wherein the fracturing fluid thickener is prepared through steps of:
(1) dissolving diethanolamine and thionyl chloride in chloroform to obtain a diethanolamine solution and a thionyl chloride solution, respectively; dropwise adding the thionyl chloride solution to the diethanolamine solution in an ice bath and then heating to perform a reaction; and after the reaction is completed, cooling the reaction mixture to produce an intermediate isolating the intermediate; and
(2) mixing the intermediate with an unsaturated $C_{17}$-$C_{21}$ fatty acid amidopropyl dimethylamine to produce a mixture; dissolving the mixture with ethanol; reacting the reaction mixture under heating; filtering the reaction mixture to obtain a filtrate; and distilling the filtrate under vacuum to produce the fracturing fluid thickener.

3. A method of preparing the fracturing fluid thickener of claim 1, comprising:
(1) dissolving diethanolamine and thionyl chloride in chloroform to obtain a diethanolamine solution and a thionyl chloride solution, respectively; dropwise adding the thionyl chloride solution to the diethanolamine solution in an ice bath and then heating to perform a reaction; after the reaction is completed, cooling the reaction mixture to produce an intermediate isolating the intermediate; and
(2) mixing the intermediate with an unsaturated $C_{17}$-$C_{21}$ fatty acid amidopropyl dimethylamine to produce a mixture; dissolving the mixture with ethanol; reacting the reaction mixture under heating; filtering the reaction mixture to obtain a filtrate; and distilling the filtrate under vacuum to produce the fracturing fluid thickener.

4. The method of claim 3, wherein in step (1), a reaction temperature is 30-50° C.; a reaction time is 4.5-5.5 h; and a molar ratio of diethanolamine to thionyl chloride is 1:(2.0-2.4).

5. The method of claim 3, wherein in step (2), a reaction temperature is 70-90° C.; a reaction time is 23.5-24.5 h; and a molar ratio of the intermediate to the unsaturated fatty acid amidopropyl dimethylamine is 1:(2.0-2.2).

6. The method of claim 4, wherein in step (1), the reaction temperature is 35-45° C. and the reaction time is 4.8-5.2 h.

7. The method of claim 6, wherein in step (1), the reaction temperature is 40° C. and the reaction time is 5 h.

8. The method of claim 5, wherein in step (2), the reaction temperature is 75-85° C. and the reaction time is 23.8-24.2 h.

9. The method of claim 8, wherein in step (2), the reaction temperature is 80° C. and the reaction time is 24 h.

10. The method of claim 3, wherein the unsaturated fatty acid amidopropyl dimethylamine is N,N-dimethyloleoamide propylamine or erucamide propyl-N, N-dimethylamine.

11. The method of claim 4, wherein the unsaturated fatty acid amidopropyl dimethylamine is N,N-dimethyloleoamide propylamine or erucamide propyl-N, N-dimethylamine.

12. The method of claim 5, wherein the unsaturated fatty acid amidopropyl dimethylamine is N,N-dimethyloleoamide propylamine or erucamide propyl-N, N-dimethylamine.

13. A method for recovering the fracturing fluid thickener of claim 1, comprising:
   (1) subjecting a fracturing fluid containing the fracturing fluid thickener of claim 1 to gel breaking to produce a gel-breaking product;
   (2) adding an acid solution to the gel-breaking product obtained in step (1) for phase separation; and
   (3) collecting an upper solid phase to recover the fracturing fluid thickener.

14. The method of claim 13, wherein the acid solution comprises hydrogen chloride, sulfuric acid, phosphoric acid or carbonic acid.

15. The method of claim 14, wherein the acid solution comprises hydrogen chloride, and an amount of hydrogen chloride is 2-6% by weight of the gel-breaking product.

16. The method of claim 15, wherein the amount of hydrogen chloride is 6% by weight of the gel-breaking product.

* * * * *